(12) United States Patent
Pang

(10) Patent No.: US 8,584,323 B2
(45) Date of Patent: Nov. 19, 2013

(54) DEVICE FOR SECURING RESILIENT CORD

(76) Inventor: Ah San Pang, Singapore (SG)

( * ) Notice: Subject to any disclaimer, the term of this patent is extended or adjusted under 35 U.S.C. 154(b) by 146 days.

(21) Appl. No.: 13/124,386

(22) PCT Filed: Oct. 16, 2008

(86) PCT No.: PCT/SG2008/000399
§ 371 (c)(1),
(2), (4) Date: Apr. 14, 2011

(87) PCT Pub. No.: WO2010/044747
PCT Pub. Date: Apr. 22, 2010

(65) Prior Publication Data
US 2011/0197397 A1    Aug. 18, 2011

(51) Int. Cl.
*F16G 11/00* (2006.01)

(52) U.S. Cl.
USPC ........................................ 24/132 R

(58) Field of Classification Search
USPC ............. 24/132 R, 132 AA, 132 WL, 66.9; 114/101, 114, 115, 218, 381; 188/65.4; 182/5; 604/174, 177–180
See application file for complete search history.

(56) References Cited

U.S. PATENT DOCUMENTS

| | | | | |
|---|---|---|---|---|
| 2,333,869 | A | * | 11/1943 | Larkin ................... 403/396 |
| 3,942,528 | A | * | 3/1976 | Loeser ................... 604/174 |
| 4,027,748 | A | * | 6/1977 | Persson ................. 188/65.4 |
| 4,029,103 | A | * | 6/1977 | McConnell ............ 604/179 |
| 4,493,134 | A | * | 1/1985 | Karr .................... 24/132 WL |
| 4,999,885 | A | * | 3/1991 | Lee ....................... 24/586.1 |
| 5,316,246 | A | * | 5/1994 | Scott et al. ............. 248/68.1 |
| 5,382,239 | A | * | 1/1995 | Orr et al. ................ 604/177 |
| 5,477,593 | A | | 12/1995 | Leick |
| 5,916,199 | A | * | 6/1999 | Miles .................... 604/174 |
| 6,001,081 | A | * | 12/1999 | Collen ................... 604/174 |
| 6,119,318 | A | | 9/2000 | Maurer |
| 7,198,066 | B2 | * | 4/2007 | Kagenow ............... 138/110 |
| 7,571,744 | B2 | * | 8/2009 | Zia et al. ................. 138/106 |
| 2009/0045010 | A1 | * | 2/2009 | Jordan ........................ 182/5 |
| 2010/0038199 | A1 | * | 2/2010 | Wengreen ............. 191/12 R |
| 2010/0050397 | A1 | * | 3/2010 | Kohler ................... 24/129 R |

FOREIGN PATENT DOCUMENTS

JP   2000300680   10/2000

* cited by examiner

*Primary Examiner* — James Brittain
(74) *Attorney, Agent, or Firm* — Enshan Hong; Kent H. Cheng; VLP Law Group LLP

(57) ABSTRACT

The invention provides a device for securing resilient cord and a method for using the same. The devise comprising a channel for housing a cord whereby the channel has a wall and is curved to provide a path for the cord that is neither straight nor constricting such that when the device is used to secure the cord the wall of the channel provides a frictional force on the cord under tension.

8 Claims, 7 Drawing Sheets

DEVICE FOR SECURING RESILIENT CORD

PRIORITY CLAIM

This is a U.S. national stage of application No. PCT/SG2008/000399, filed on Oct. 16, 2008.

FIELD OF THE INVENTION

The present invention generally relates to means for securing resilient cords in place. In particular the invention relates to management of resilient cord such as tubing used in the food, pharmaceutical and medical industries.

BACKGROUND INFORMATION

Known devices for securing cords such as cable ties or straps or clips often require constricting or pinching the cord to hold it in place. Where a cord is a tube it is generally used to convey fluids such as food, chemicals, medicines, gases and such. Securing a tube designed to convey fluids by constriction could disrupt the tube's main function by narrowing the lumen, and reducing or blocking the flow of fluids. For this reason such tubing are often secured by glue or other chemical adhesiyes in a sticking or fixing plaster. Such glue or other chemical adhesives may be used only once and usually are to secure the tube or tubes permanently in one place. Often the adhesive will damage the tube. They are unsuitable in situations where the surface of the tubing should not be damaged or altered, and where the segments to be held together have to be changed now and then.

Medical tubes are usually formed of materials that are relatively soft or of low durometer readings such as, for example, silicone rubber. The material commonly used results in the tube having a resilient elastic quality that are prone to stretch. Clips which can hold the tubing snugly, without constricting the lumen are available. However, the tubes tend to slip out of position when there is tension on the tubing. Since the tubing is elastic, it elongates under tension and becomes a thinner structure. As a result, the snug fit of the clip around the tube is lost and the clip slips out of position.

An example of this is depicted in FIG. 1, where 1a shows a tubing clip and a hollow elastic tubing marked X where it is desirable to have the tube clamped; 1b shows the clip holding the tubing snugly at the proper place marked X; 1c shows the tubing becoming thinner when it elongates under tension. The clip no longer holds onto the tubing and slips out of position by gravity or an extraneous force; and 1d shows that the clip has displaced from proper place marked X when there is no more tension on the tube. Where a clip moves from a desirable place to have the tube clamped to somewhere else on the tube it can result in either
 a) the tube being too tight and impinging on the entry point of the tube into the body which is likely to be uncomfortable or painful for the patient; or
 b) the tube could become too loose increasing the possibility of the tube being dislodged or coming out which may cause pain and discomfort or unnecessary complications.

Frequently, there is a need to bundle two or more tubes together particularly in a medical setting. It is often important that these tubes do not become tangled or intertwined to avoid any unnecessary complications and/or time consuming untangling by medical personnel.

The preceding discussion of the background to the invention is intended only to facilitate an understanding of the present invention. It should be appreciated that the discussion is not an acknowledgment or admission that any of the material referred to was part of the common general knowledge as at the priority date of the application.

There is a need for a device which can secure segments of resilient tubing and may ameliorate some or all of the problems of prior art.

SUMMARY OF THE INVENTION

Throughout this document, unless otherwise indicated to the contrary, the terms "comprising", "consisting of", and the like, are to be construed as non-exhaustive, or in other words, as meaning "including, but not limited to".

In accordance with a first aspect of the present invention there is provided a device for securing resilient cord comprising a channel for housing a cord whereby the channel has a wall and is curved to provide a path for the cord that is neither straight nor constricting such that when the device is used to secure the cord the wall of the channel provides a frictional force on the cord under tension.

Such a device may be advantageous in that: the design is unlikely to reduce or block flow of fluids as the lumen of the tube is not constricted and is unlikely to be narrowed; it is unlikely that the device will shift when there is tension which changes the dimensions of the tube; similarly it is unlikely that the surface of the tubing will be altered by the use of the device;

Preferably the device may include at least two curved channels; the at least two curved channels intersect at a location whereby when the at least two curved channels house a cord, the cords may contact each other at the location where the at least two curved channels intersect.

Preferably the device may form a void at the location where the at least two curved channels intersect, the void providing a larger space for housing the cord than the at least two curved channels.

Preferably the curved channel may be formed by two hinged portions having U shaped passages extending within and along both portions whereby the U shaped passage on the first portion connects with the U shaped passage on the second portion to form the curved channel.

In one embodiment the device may be interconnected with at least a second device having a further curved channel adapted to secure a cord such that a plurality of cords can be secured within the interconnected devices. This may have the advantage of minimizing any unnecessary complications from tangled tubes and/or time consuming untangling by medical personnel.

The device may further include a lock.

The device may be easily removed from one segment of tubing and re-applied to other segments of tubing. Preferably the lock may include at least two locking tunnels held together with a locking pin.

In accordance with another aspect of the present invention there is provided a method of securing resilient cord comprising the steps of:
 a) placing a resilient cord in a curved open passage of a first portion of a device;
 b) placing a second portion. over the first portion housing the resilient cord; and
 c) securing the first and second portion together whereby the open passage forms a curved channel with the second portion, the curved channel having a wall that can provide a frictional force on the cord under tension securing the Cord at a desired location.

In a preferred embodiment before step b a second resilient cord is placed in a second curved open passage whereby the first and second resilient cord contact each other at one location along the first and second passage.

In a preferred embodiment the second resilient cord is crossed over the first resilient cord to form a hitch or at least one hitch.

BRIEF DESCRIPTION OF THE DRAWINGS

The invention will be better understood by reference to the following drawings in which.

DETAILED DESCRIPTION OF THE PREFERRED EMBODIMENTS OF THE INVENTION

Figure 1:
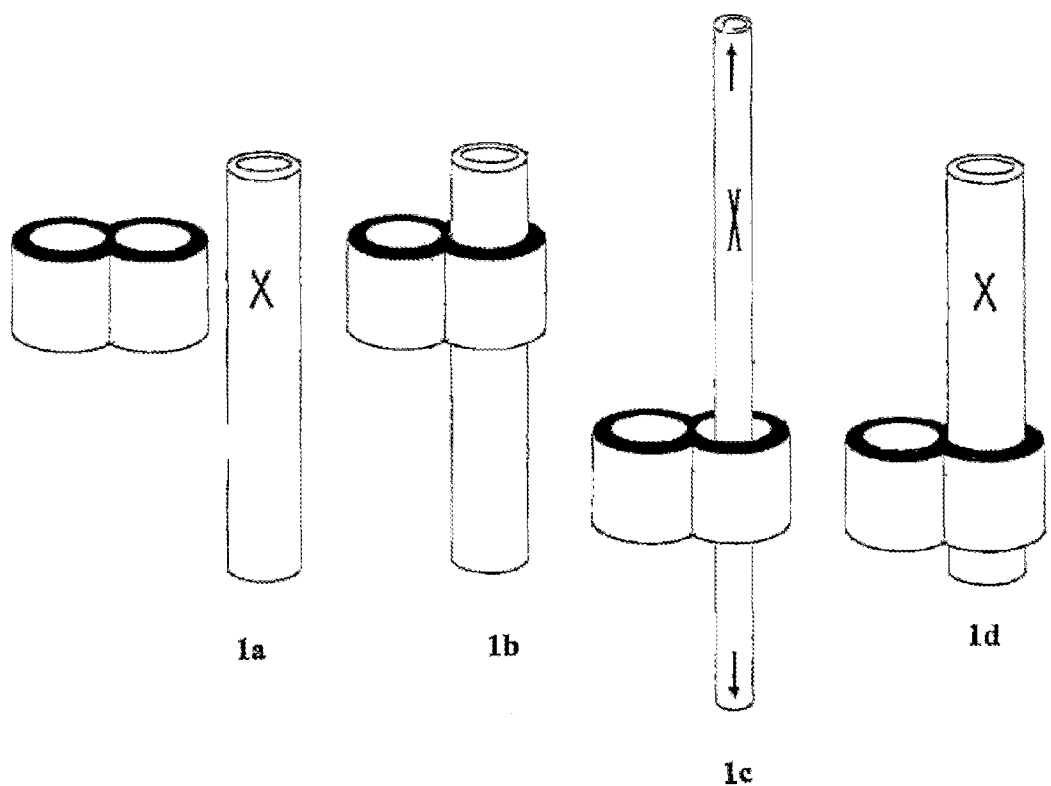
FIG. 1 is an illustration demonstrating one of the difficulties of using a clip of the prior art to secure a resilient tube.
Figure 2:
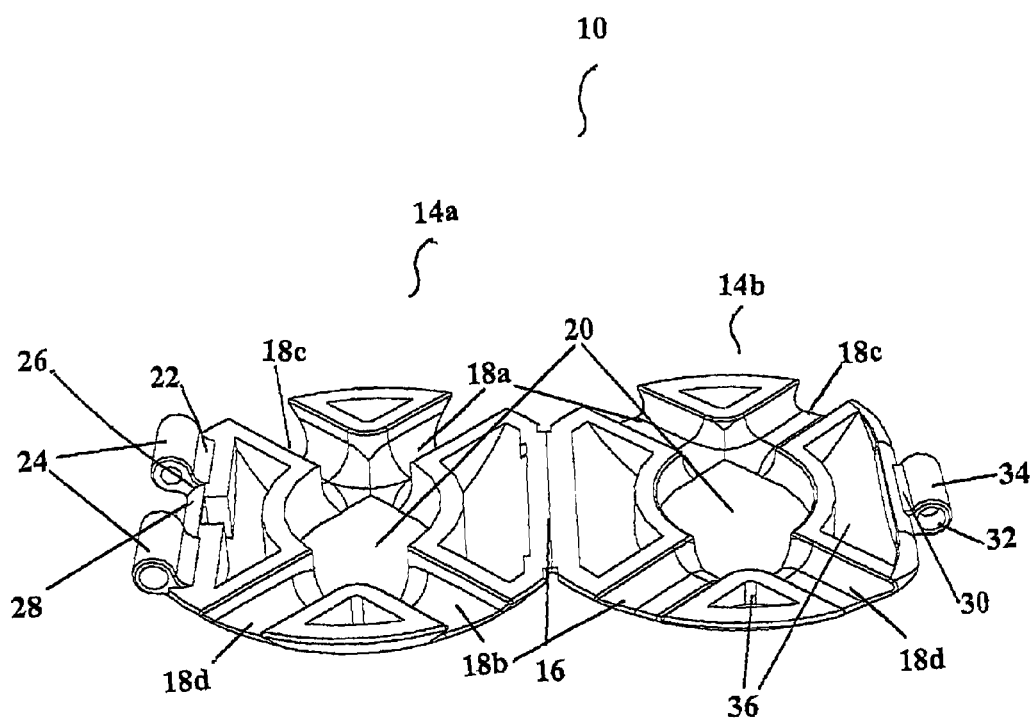
FIG. 2 is an illustration of the device in an open position according to a first embodiment of the invention.

Referring to FIG. 2 in accordance with a first embodiment of a device for securing resilient cord 10 comprises a casing having two portions 14 with a depth. Both portions 14 are of a roughly octagonal shape connected at a hinge 16 along one of the eight sides. Each portion comprises four U shaped open passages 18 the floor of which is in a plane substantially parallel to the plane in which the hinge 16 sits and the edges of the U shaped open passages 18 falling roughly within the same plane as the plane in which the hinge 16 sits. The first U shaped open passage 18a opens at one of the eight sides joining the hinge 16 side with the remaining three U shaped open passages 18b, 18c and 18d opening at the sides alternating with the side on which the first U shaped open passage 18a starts. Each of the U shaped open passages 18 starts at one side and extends along into the portion 14 converging in a void 20 roughly at the center of the portion 14. U shaped open passage 18a is preferably out of alignment with U shaped open passage 18b. U shaped open passage 18a and 18b forms a curved passage with a space adapted to hold a resilient tube, the curved passage being disrupted by the void 20. Similarly; U shaped open passage 18c and 18d forms a curved passage with a space adapted to hold a resilient tube, the curved passage being disrupted by the void 20.

On the first portion 14a at the side opposite the hinge 16 side two projections 22 extend at an angle away from the side and almost transverse to the plane in which the hinge 16 sits. The projections 22 end with a tube 24 lying across the top of the projection 22. The tube has a central longitudinal axis with an axial bore parallel to the plane in which the hinge 16 sits. The projection 22 and the tube form a locking tunnel 26. The two locking tunnels 26 are separated by a gap 28. The gap 28 is roughly along the center of the side opposite the hinge 1.6 side of the roughly octagonal shape. On the second portion 14b at the side opposite the hinge 16 side one projection 30 extend at an angle away from the side and almost transverse to the plane in which the hinge 16 sits. The projection 30 ends with a tube 32 lying across the top. The tube 32 has a central longitudinal axis with an axial bore parallel to the plane in which the hinge 16 sits. The projection 30 and the tube 32 form an opposite locking tunnel 34. The opposite locking tunnel 34 is roughly along the center of the side, opposite the hinge 16 side of the roughly octagonal shape.

In the first embodiment the segments around the void 20 between the U shaped open passages 18 are hollowed openings 36 to reduce the expense and weight of making these segments solid. The casing is made of a hard and inflexible material such as glass or ceramic or metal or plastic for example nylon, polypropylene or polyethylene or the like. The embodiment of FIG. 2 is formed of polypropylene. It would be understood that where a patient has medical tubes extending from their body it would be desirable to have minimal additional weight attached to secure the tubes.

Figure 3:
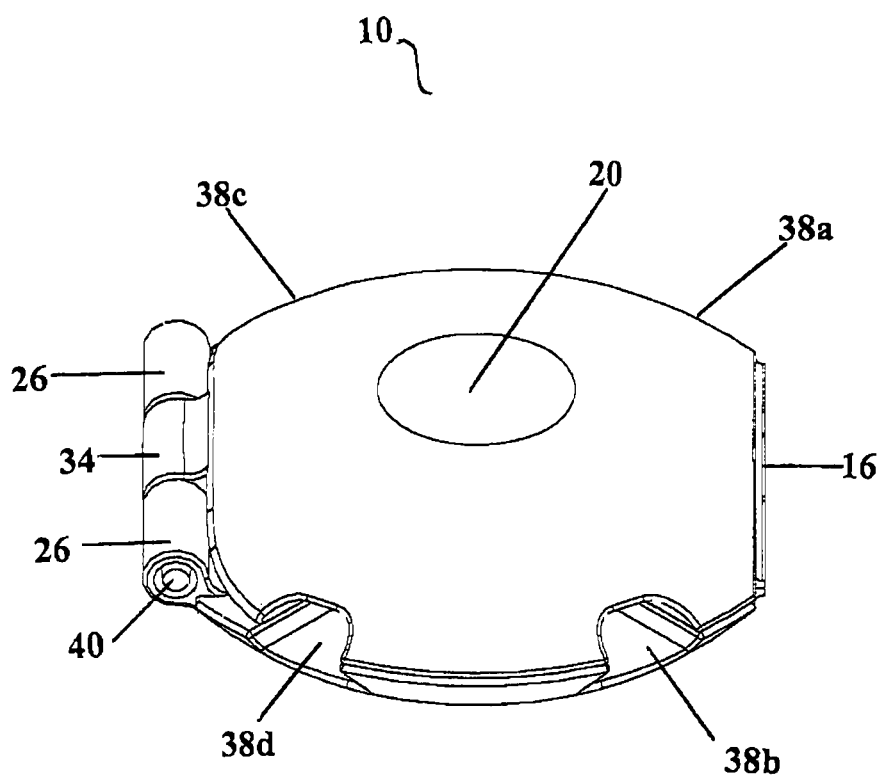
FIG. 3 is an illustration of the device in a closed position according to a first embodiment of the invention.

Referring to FIGS. 2 and 3 when the two portions 14 of the first embodiment are brought together about the hinge 16, the four U shaped open passages 18 on the first portion 14a connect with the four U shaped open passages 18 on the second portion 14b to form four channels 38 converging in the void 20. These channels provide a snug but non-constricting and non-kinking fit for the cord. Channel 38a and channel 38b are out of alignment forming a curved channel disrupted by the void 20. Similarly, Channel 38c and channel 38d are out of alignment forming a curved channel disrupted by the void 20. The opposite locking tunnel 34 fits snuggly in the gap 28 between the two locking tunnels 26. The three locking tunnels 26, 34 form a through axial bore along the central longitudinal axis, the axial bore adapted to receive a locking pin 40 therein.

Figure 4:
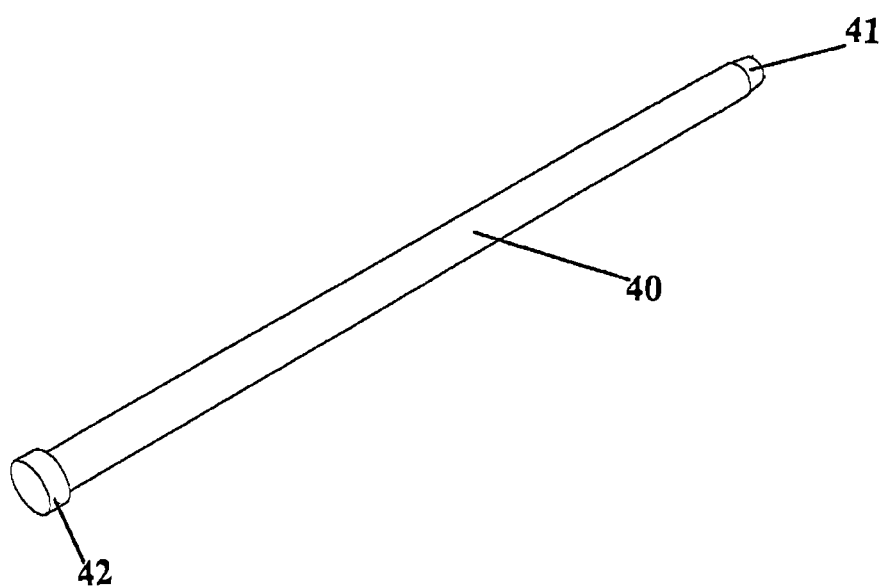
FIG. 4 is an illustration of the locking pin according to the first, second or third embodiment of the invention.

Referring to FIG. 4 the locking pin 40 of the first embodiment is illustrated as having a leading end 41 for inserting into the through axial bore along the central longitudinal axis formed by the three locking tunnels 26, 34 and a head 42 for stopping the locking pin 40 from falling out. The locking pin 40 should be a tight fit in the axial bore to ensure the locking function. It can be understood that in situations where the locking pin 40 is not as tight a fit however the device 10 is fixed in a position whereby an imaginary line can be extended from the leading end 41 to he substantially perpendicular to the around and the head 42 is facing the sky that gravity will form a lock to keep the locking pin 40 in place. Alternatively the locking pin can be formed into a circle or a folded structure (not shown) such that the leading end 41 and the head 42 are connected or in close proximity to ensure that the first and second portion 14a and 14b remain together or locked.

Figure 5:
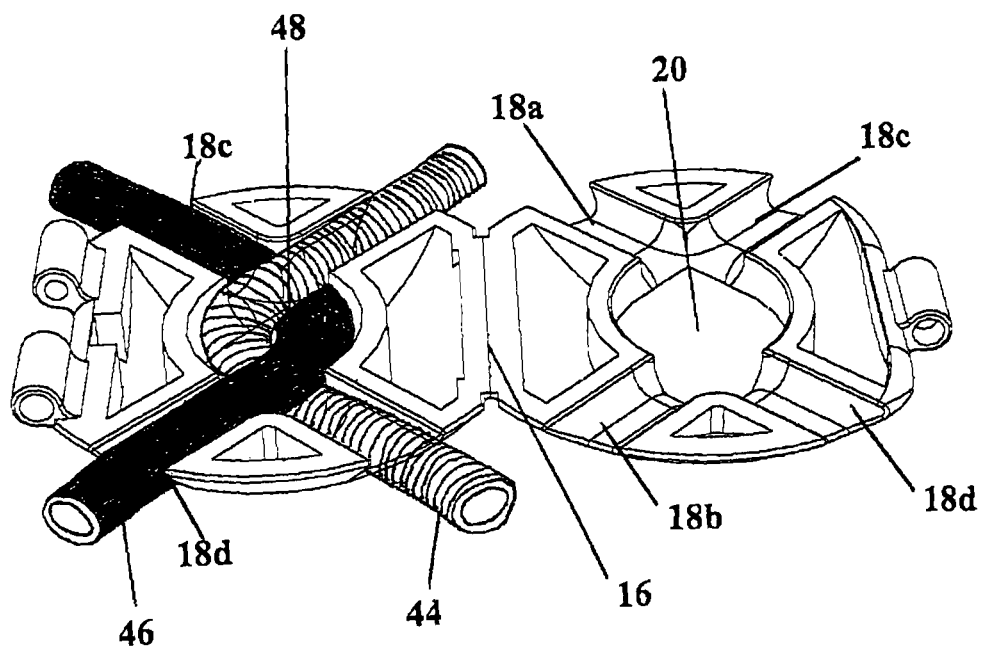
FIG. 5 is an illustration of the device in an open position with the resilient cord according to a first embodiment of the invention.

To use the device for securing resilient cord according to the first embodiment in FIG. 5 a first cord 44 enters the U shaped open passage 18a and is bent at an angle whereby the first cord 44 is not constricted and is passed out the U shaped open passage 18b. This results in the first cord 44 lying with a bend in the central void 20 and angled such that one portion of the first cord 44 sits in the first U shaped open passage 18a and another portion of the first cord 44 sits in the second U shaped open passage 18b. A second cord 46 enters the third U shaped open passage 18c and is bent at an angle whereby the second cord 46 is not constricted and is passed out the fourth U shaped open passage 18d. This results in the second cord 46 lying either with a bend or a hitch 48 in the central void 20 and angled such that one portion of the second cord 46 sits in the third U shaped open passage 18c and another portion of the second cord 46 sits in the fourth U shaped open passage 18d.

The second cord 46 may engage the first cord 44 to form a hitch 48 within the void 20. The hitch 48 is formed by crossing the first 44 and second 46 cords over each other such that they bend over each other at a common central point There may be more than one hitch 48. Alternatively, the operator may not want the first and second cords 44 and 46 to engage each other in a hitch 48 but to lie side by side (not shown) or on top of each other (not shown).

Figure 6:
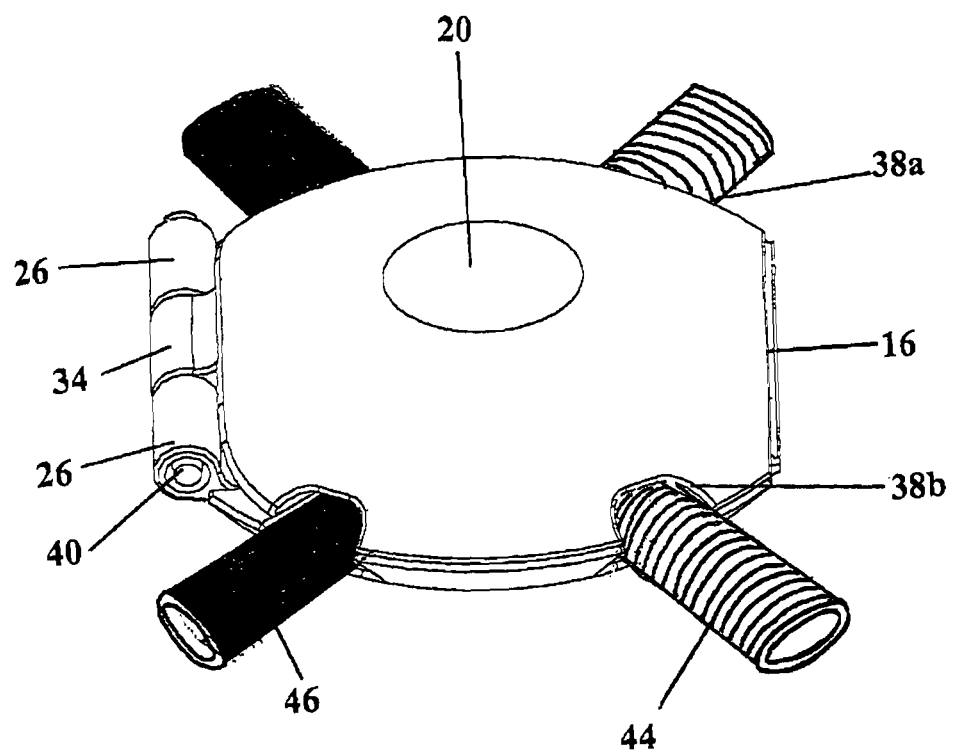
FIG. 6 is an illustration of the device in a closed position with the resilient cord according to a first embodiment of the invention.

Referring to FIG. 6 when the second portion 14b of the device 10, which is conveniently hinged to the first portion 14a via the hinge 16, is closed the cords 44, 46 or tubes are secured. The device 10 is kept in the closed position by the locking pin 40. The two segments of cord 44 and 46, in this case hollow elastic. tubing are secured together. The U shaped open passages 18 form channels 38 around the cords 44, 46. The first cord 44 has a portion in channel 38a and a second portion in 38b with a central portion between these that sits within the void 20. Similarly the second cord 46 has a portion in channel 38c and a second portion in 38d with a central portion between these that sits within the void 20. The two central portions of the first and second cords 44 and 46 sitting within the void 20 are lying bent side by side or one on top of the other or are engaged in a hitch 48.

The channels 38 provide a snug but non-constricting and non-kinking fit for the cords 44, 46. The channels 38a and 38b are out of alignment forming a curved channel disrupted by the void 20. Similarly, the channels 38c and 38d are out of alignment forming a curved channel disrupted by the void 20. Even when the cord or tubing is under tremendous tension and becomes a thin straight cord, the walls of the curved channel provides frictional contact with a part of the cord due to the misalignment of the channels. Therefore, the device 10 does not slip out of position. In fact, the greater the tension on the cord or tubing, the stronger the channel 38 holds onto the cord or tubing.

The void 20 provides a larger space for the bends or the hitch 48 formed by the first and second tube 44 and 46 to stay. At the void 20, the first and second tube 44. and 46 can engage each other to form a hitch 48 or the bends can lie in a side by side arrangement. The void 20 provides a snug but non-constricting and non-kinking fit for the hitch 48 or a bend to stay. The hitch 48 being a half-knot and larger than the channel 38, cannot escape from the channel 38 or device 10. Hence, it is secured in place. Tension in any tubing or cord will not cause the device to move relative to the other tubing because of the fiction of the channels 38 and the larger space in the void 20. In fact, in the hitch formation the greater the tension on the first resilient cord 44, the stronger the device 10 holds onto the second resilient cord or tube 46.

Figure 7:
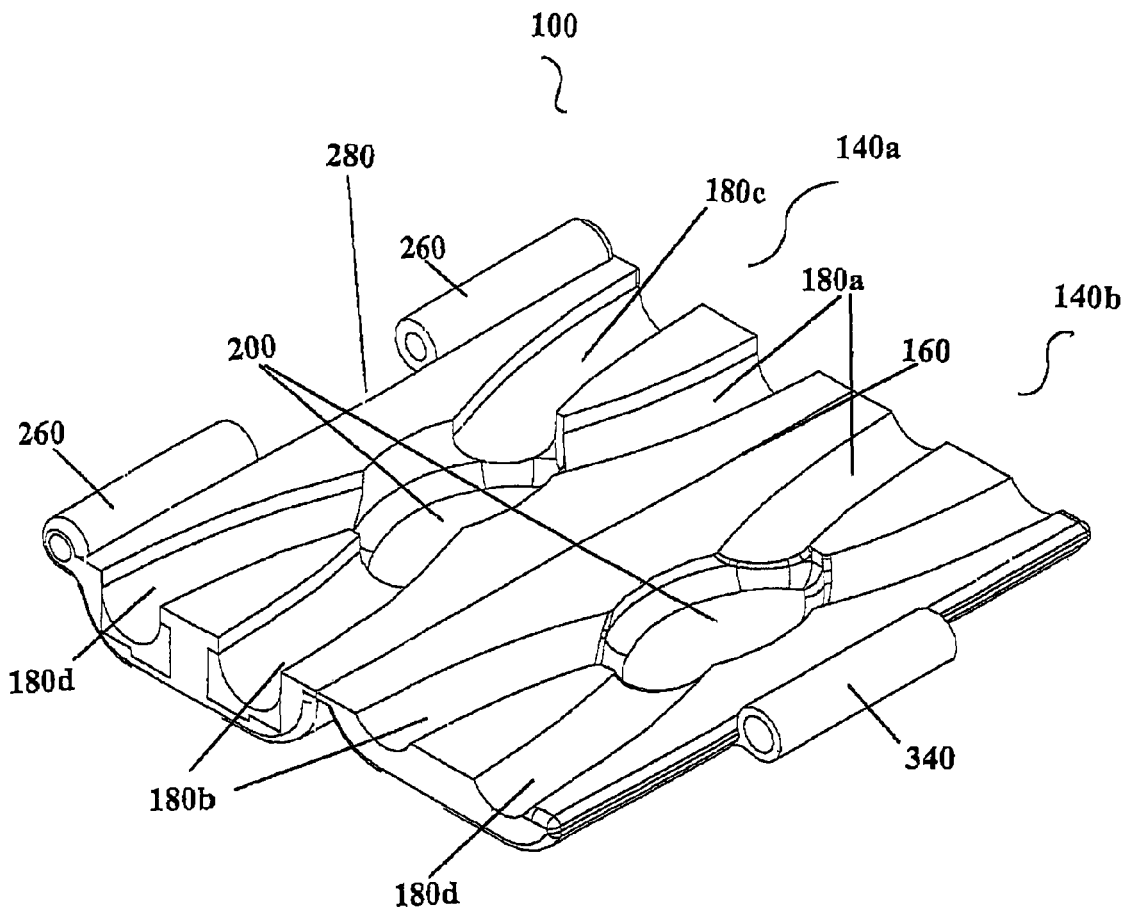
FIG. 7 is an illustration of the device in an open position according to a second embodiment of the invention.

Referring to FIG. 7 in accordance with a second embodiment, the mis-alignment of the first and second channel and third and forth channel is less acute. This is achieved by the misalignment of the first U shaped open passage 180a with the second U shaped open passage 180b and correspondingly the misalignment of the third U shaped open passage 180c with the fourth U shaped open passage 180d. In accordance with a second embodiment of a device for securing resilient cord 100 comprises two portions 140 with a depth. Both portions are of a roughly rectangular shape connected at a hinge 160 along one of the longer sides of the roughly rectangular shape. Each portion comprises four U shaped open passages 180 the floor of which is in a plane substantially parallel to the plane in which the hinge 160 sits and the upper edges of the U shaped open passages 180 falling roughly within the same plane as the plane in which the hinge 160 sits. The first and third U shaped open passage 180a and 180c opens at one of the shorter sides of the roughly rectangular shape joining the hinge 160 side with the remaining two second and fourth U shaped open passages 180b and 180d opening at the opposite shorter side of the roughly rectangular shape from which the first and third U shaped open passages 180a and 180c starts. Each of the U shaped open passages 180 starts at one of the two shorter sides of the roughly rectangular shape and extends along into the portion 140 converging in a void 200 roughly at the center of the portion 140. U shaped open passage 180a is out of alignment with U shaped open passage 180b. U shaped open passage 180a and 180b forms a space adapted to hold a resilient tube. Similarly, U shaped open passage 180c is out of alignment with U shaped open passage 180d. Similarly, U shaped open passage 180c and 180d forms a space adapted to hold a resilient tube.

On the first portion 140a of the second embodiment at the side opposite the hinge 160 side two tubes with a central longitudinal axis with an axial bore parallel to the plane in which the hinge 160 sits form a locking tunnel 260. The two locking tunnels 260 are separated by a gap 280. The gap is roughly along the center of the side opposite the hinge 160 side of the roughly rectangular shape. On the second portion 140b at the side opposite the hinge 160 side one tube with a central longitudinal axis with an axial bore parallel to the plane in which the hinge 160 sits forms an opposite locking tunnel 340. The opposite locking tunnel 340 is roughly along the center of the side opposite the hinge 160 side of the roughly rectangular shape.

The second embodiment is used in a similar manner as the first embodiment as described above. Such that the misalignments of the channels where the cord or tube sit in the device 100 provides a frictional contact with a part of the cord when it is stretched ensuring the cord or tube remains in place. Further the void 200 provides a space larger than the channels to ensure the hitch or bend remains within the void 200 and is not easily pulled out such that the cord or tube may be secured in place.

In a third embodiment (not shown), the hinge 16, 160 between the first portion 14a, 140a and the second portion 14b, 140b is replaced by a pair of locking tunnels 26, 260 on the second portion 14b, 140b and an opposite locking tunnel 34, 340 on the first portion 14a, 140a such that the first and second portion can be interconnected by aligning the locking tunnels on both portions side by side, inserting a further locking pin through the bores formed in the locking tunnels in a similar manner as described above. This configuration will allow several devices 10, 100 to be interconnected together as modular units to hold multiple pairs of cords or tubes at the same time in a side by side arrangement. In this way a plurality of 2, 3 or more cords can be secured together in an orderly manner, minimising the chance of the tubes becoming tangled or intertwined. This will have the advantage of minimizing any unnecessary complications from tangled tubes and/or time consuming untangling by medical personnel.

Various embodiments and extra features are envisioned in relation to the present invention. They include:
  The device, when made from an appropriate metal or material, can be used as a clamp in the rope and rigging industries.
  It is possible to have multiple channels within one device.
  It will be obvious to those skilled in the art, that there are many options for locking the device besides the locking pin.
  The first and second portion may have the same proportions or unequal dimensions. The device can also take many shapes.
  The channel may be formed in one portion alone while the other portion may act as a lid with no passages formed therein.
  The dimensions of the void, where the channels meet could be changed to accommodate an increase in the number of twists or hitches by the tube segments.

Although the device is suited to secure elastic hollow tubing, it can be used for any flexible cables, ropes and cords which are not hollow.

The device can be, made ornamental for use in the clothing and fashion industries e.g. with a bolo tie or shoe laces.

Modifications and variations as would be apparent to a skilled addressee are deemed to be within the scope of the present invention.

I claim:

1. A device for securing resilient cords comprising at least two channels, wherein the at least two channels intersect at a location, each of at least two channels is provided for housing one of the cords, each of the at least two channels has a wall and is curved to provide one of the cords a path that is neither straight nor constricting such that when the device is used to secure the cords, the wall of each of channels provides a frictional force on one of the cords under tension, whereby when each of the at least two channels houses one of the cords, the cords may contact each other at the location where the at least two channels intersect.

2. The device of claim 1, wherein at the location where the at least two curved channels intersect, a void is formed, the void providing a larger space for housing the cords than the at least two curved channels.

3. The device of claim 1 wherein each of the at least two curved channels is formed by two hinged portions having U shaped passages extending within and along both portions whereby the U shaped passage on the first portion connects with the U shaped passage on the second portion to form each of the at least two curved channels.

4. The device of claim 1 wherein the device is interconnected with at least a second device having a further curved channel adapted to secure a cord such that a plurality of cords can be secured within the interconnected devices.

5. The device of claim 1 further comprising a lock.

6. The device of claim 5 wherein the lock comprises at least two locking tunnels held together with a locking pin.

7. A method of securing resilient cords comprising the steps of:

a. placing a first resilient cord at an angle whereby the first resilient cord is not constricted in a first curved open passage of a first portion of a device and placing a second resilient cord in a second curved open passage of the first portion of the device, wherein the first and second resilient cords contact each other at one location along the first and second passages;

b. placing a second portion over the first portion housing the resilient cords; and c. securing the first and second portion together whereby each of the open passages forms a curved channel with the second portion, the curved channel having a wall that can provide a frictional force on one of the cords under tension securing the one of the cords at a desired location whereby the one of the cords is not constricted.

8. The method as claimed in claim 7, wherein the second resilient cord is crossed over the first resilient cord to form a hitch.

* * * * *